United States Patent [19]

Cowle et al.

[11] Patent Number: 4,921,544

[45] Date of Patent: May 1, 1990

[54] ELECTROPHORETIC CLEANER AND STERLIZER

[75] Inventors: Anthony J. Cowle; Paul J. Cowle; Gregory J. Cowle; Joffre B. Cowle, all of Chatswood, Australia

[73] Assignee: Baremek Pty. Limited, Willoughby, Australia

[21] Appl. No.: 140,152

[22] Filed: Dec. 30, 1987

Related U.S. Application Data

[62] Division of Ser. No. 755,610, Jul. 16, 1985, Pat. No. 4,732,185.

[51] Int. Cl.$^5$ .............................................. B08B 3/10
[52] U.S. Cl. .......................................... 134/1; 134/27; 134/42; 422/20; 422/128
[58] Field of Search ........................... 134/1, 2, 27, 42; 422/20, 128

[56] References Cited

U.S. PATENT DOCUMENTS

| | | | |
|---|---|---|---|
| 4,187,868 | 2/1980 | Rudolphi | 134/1 |
| 4,382,824 | 5/1983 | Halleck | 134/1 |

*Primary Examiner*—Asok Pal
*Attorney, Agent, or Firm*—Ladas & Parry

[57] ABSTRACT

An electrophoretic technique and apparatus for decontamination and sterilizing of contact lenses are provided. The lenses are placed in respective perforated containers and inserted in a buffer solution of suitable pH value. An electric field is established in the solution by a pair of spaced electrodes. Contaminants on the lenses become charged and are attracted to a respective electrode, thereby cleaning and sterilizing the lenses.

3 Claims, 2 Drawing Sheets

ELECTROPHORETIC CLEANER AND STERLIZER

This is a divisional of co-pending application Ser. No. 755,610 filed on July 16, 1985, now U.S. Pat. No. 4,732,185

The present invention relates to electrophoretic cleaning and sterilizing. In particular, the invention is directed to an electrophoretic technique and apparatus for decontamination and sterilizing of contact lenses.

Known methods of cleaning and sterilizing contact lenses have not proved to be entirely successful in removing contaminating products of tear fluid, especially protein debris. The popular "boiling" method is more of a sterilizing technique rather than a decontamination process. The use of enzyme tablets, which themselves comprise protein, has also proved inadequate for complete removal of protein debris. Detergents have also been used to clean contact lenses, but such detergents can damage the lenses.

An electrophoretic decontamination technique for contact lenses was proposed in Australian patent application No 11108/83. However, in that arrangement, there was a high risk of cross-contamination between lenses. If one eye was infected, the other eye could easily become infected too from contaminants pulled from the other lens. A further disadvantage was that fluid could not be sampled for pathology for each eye individually.

Moreover, there was no disclosure in application No 11108/83 of a suitable buffer solution nor of a suitable pH for the buffer solution.

It is an object of the present invention to provide an improved apparatus for decontamination and sterilization of contact lenses and a buffer solution for use therein.

The present invention utilizes the principle of electrophoresis. That is, when an electric field is set up between two electrodes in a solution or suspension, negatively-charged particles in solution or suspension move towards the positive electrode (anode) and positively-charged particles move in the opposite direction towards the cathode. The electrical charges borne by particles of colloidal size, for example proteins, may arise from charged atoms or groups of atoms that are part of the structure of the particle itself, from ions which are adsorbed from the liquid medium, and from other causes. Thus, if two electrodes are inserted on opposite sides of a tube containing a solution of proteins, the proteins will become charged and move in one direction to the oppositely charged electrode.

In the present invention, a protein contaminated contact lens is placed within a perforated container and inserted in a buffer solution in an electric field set up by a pair of electrodes in the solution. The contamination, which comprises mostly protein material, becomes charged and migrates through the solution under the action of the electric field to a corresponding electrode. The lens is thereby cleaned and sterilized "electrically".

In one broad form therefore, the present invention provides apparatus for decontaminating and sterilizing contact lenses by electrophoresis, said apparatus comprising a respective container for each lens adapted to hold a buffer solution; a pair of spaced electrodes within each said container and connectable to a DC power supply to form a unidirectional electric field in said buffer solution; and a lens holder for each lens insertable in a respective container, each said lens holder having a perforated compartment for housing its lens and positioning same in the electrical field in the buffer solution when the lens holder means is inserted in its respective container.

There is also provided a method of decontaminating and sterilizing a contact lens by electrophoresis, said method comprising the steps of:

(i) establishing a unidirectional electric field between two electrodes in a buffer solution, and (ii) inserting a perforated holder containing said lens in the buffer solution in the electric field between the electrodes for a predetermined time, wherein said buffer solution preferably has a pH of approximately 8.3 and comprises a dilution of a concentrate of boric acid, disodium edetate and TRIS in relative proportions of approximately 0.808M, 0.029M and 0.825M respectively.

By way of example, a preferred embodiment of the present invention will now be described with reference to the accompanying drawings in which.

Figure 1:
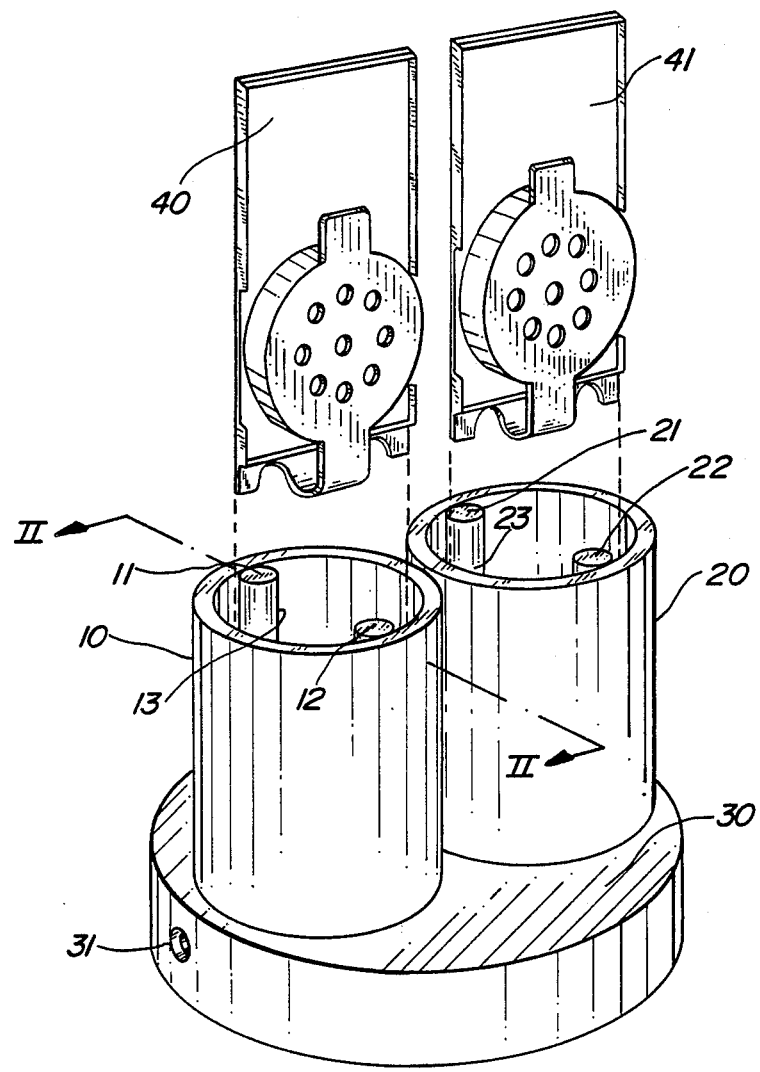
FIG. 1 is a perspective view of an embodiment of the present invention.
Figure 2:
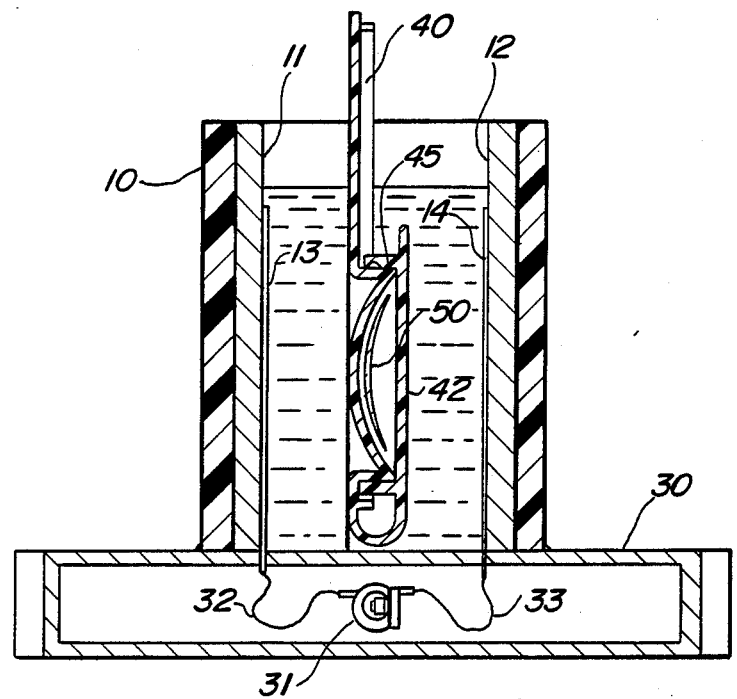
FIG. 2 is a sectional view along A—A of FIG. 1.
Figure 3:
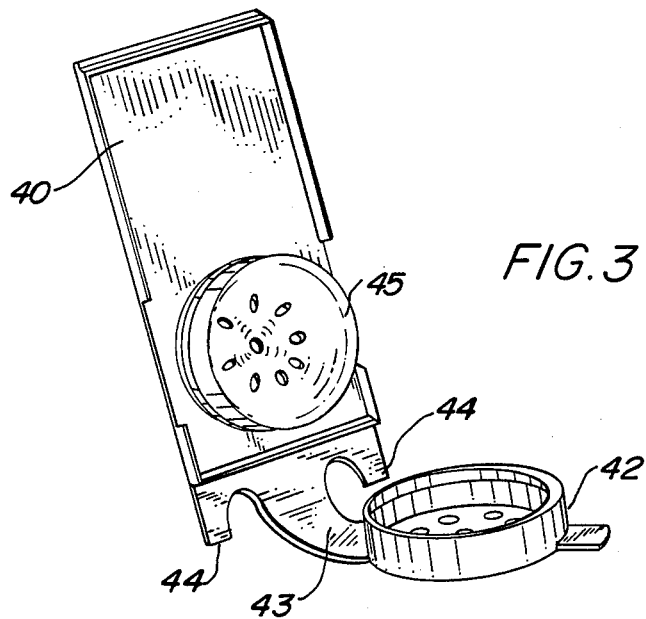
FIG. 3 is a perspective view of a lens holder of the embodiment of FIG. 1.

A preferred embodiment of the invention is illustrated in FIGS. 1 to 3, and consists of two acrylic cylindrical tubes 10, 20 mounted upright on a cylindrical base 30. Typically, the tubes have an internal diameter of 26 mm, a wall thickness of 2 mm and a length of 4 cm. A pair of posts 11, 12 (21, 22) are arranged on the internal sides of each tube 10 (20) in opposed relationship. An electrode, typically a platinum electrode, is mounted on each of the posts. For the sake of simplicity, the description will proceed in respect to tube 10 only, tube 20 being substantially identical. Thus, platinum electrodes 13, 14 are mounted on posts 11, 12 respectively, in opposed relationship. The platinum electrodes 13, 14 are connected to a DC power source via connecting wires 32, 33 and socket 31 provided on the cylindrical base 30. Typically, a DC supply is connected to socket 31 and fed directly to the electrodes 13, 14. However, further electrical processing circuits, such as voltage reduction and protection circuits can be incorporated in the cylindrical base between the socket 31 and the electrodes 13, 14. The pair of electrodes 13, 14 are wired to form an anode and a cathode in the tube.

A smooth regulated DC power supply with an output rating of 9 volts and 200 milliamps is applied to the electrodes in each tube to establish a unidirectional electrical field in the solution. For safety reasons, electrical circuitry is not incorporated in the illustrated apparatus beneath the solution; however if the fluid compartment is sealed properly, a power supply can be incorporated within the base 30 of the apparatus. If an inbuilt transformer is used, allowance should be made for heat dissipation from components and also to prevent evaporation and heating of the buffer solution.

A lens holder 40 (41) is provided for each tube. Preferably, the lens holders are labelled "left" and "right" for use in respective tubes. The presence of the posts in each tube prevent the lens holders from being aligned with the electrodes and help to keep the lenses generally perpendicular to a line joining each pair of electrodes. Such orientation facilitates the removal of contaminants from the lenses. The lens holder 40 is shown in more detail in FIG. 3, lens holder 41 being substantially identical. Preferably, the lens holder 40 is made of plastic and comprises a perforated cup portion 41 and a perforated cover 42 which together form a compartment for housing a lens. Typically, the cover 42 is made integral with the lens holder 40 and joined thereto by a neck portion 43. Lugs 44 are provided at the bottom of the lens holder 40 so that when the lens holder 40 is placed in the tube, an opening is present at the lower end to establish free communication between the two electrode compartments on either side of the lens holder in the tube.

The provision of separate tube compartments for the lenses minimizes the risk of cross-contamination and allows fluid to be sampled from each eye for pathology purposes.

Sufficient buffer solution is poured into each tube to immerse totally the lenses and electrodes. In the described embodiment, the amount required is 12 millilitres in each tube compartment. The buffer is preferably a tris-borate buffer of pH 8–9, and typically pH 8.3, formed from a 1:10 dilution of a concentrate having the following composition: boric acid 0.808M, disodium edetate 0.029M and TRIS 0.825M. The TRIS (Tromethamine) component has the following advantages:

(a) It does not absorb carbon-dioxide from the air
(b) It is miscible with and emulsifies fatty materials such as oils and waxes, i.e. it takes these substances into solution. Other inorganic buffers such as phosphate buffer will not take up calcium because calcium phosphate is insoluable.
(c) it is not incompatible with glycerol, alcohol and other organic solvents.
(d) it has been used as an emulsifying agent in cosmetic and pharmaceuticals and generally acceptable under drug legislation.

The Boric (boracic) acid has preservative and antiseptic properties, both antibacterial and antifungal. It too is generally acceptable under drug legislation.

The disodium edetate is advantageous in that it is a metal chelating agent (can take up calcium) and an anti-oxidant. It displaces carbon dioxide from metal carbonates to form hydrogen. It too is generally acceptable under relevant drug legislation.

The proportions of the components of the buffer solution can be varied to adjust the buffer pH, which preferably is 8.3 but can be between pH 8 and 9.

Advantageously, the buffer solution is prepared in concentrate form and diluted prior to use. In concentrate form, the buffer is stable for up to five years. For routine care of daily wear lenses, it is recommended that the diluted solution be renewed at weekly intervals.

Application of the unidirectional electrical field to the buffer solution results in the charging of protein and other material on the lenses, which material then migrates to a respective electrode. Since the lens is formed of material having a matrix structure with spacings greater than the size of the contaminants, e.g. protein colloids, the contaminants are able to pass through the lens itself. At the abovementioned voltage and current levels, separation is achieved typically between ten and twenty minutes.

The theory underlying the operation of the above-described apparatus is as follows.

A substance can only migrate if it contains a charge i.e., if it is ionized. A protein at a pH above its isoelectric point will move towards the anode. Its rate of migration is proportional to its degree of ionization and hence the higher the pH the faster it will migrate. Most interest is centred on amphylytes such as amino acids and proteins which migrate to the anode at pH above their isoelectric point and in the reverse direction below this.

The notion that the value of the buffer is in controlling the pH of the medium is a gross over-simplification. The buffer does indeed maintain a constant pH but it also ensures that each component will maintain a constant charge during the separation because the ionisation of each compound is stabilised and this is particularly important for amphylytes so that they will migrate under reproducable conditions.

The more concentrated the buffer solution the slower will the other components move as the current is carried by the ion present. The greater the quantity of buffer ion in relation to other ions the greater the proportion of its current they carry. Furthermore, the movement of ions surrounded by ions of opposite charge is retarded by the attraction of these ions so that increased buffer concentration reduces the migration rate of the substances to be separated. For this reason the buffer is used preferably in high dilution with its components in low ionic strengths. The pH and buffer composition used enables the protein to remain soluble in solution where all the components are present as anions. The best pH for any given mixture is a matter for enpirical investigation easily carried out by a person skilled in the art. The pH chosen is the most desirable for the maximum separation of all the components present.

During the electrophoretic separation electro-endosmotic flow of water carrying the buffer salts moves in the opposite direction to the migrating components. Neutral molecules are also carried in the endosmotic flow.

Low voltage only is required for separation of large protein molecules, nucleac acids and enzymes as well as simple molecules such as amino acids and medium sized molecules such as peptides and nucleotides. The principle protein contaminents are those of the tear secretion such as albumin and the globulines. Effective separation of virus particles and bacteria can be attributed to the protein components of the walls of these micro-organisms. Inorganic ions such as calcium deposits are also removed. The pore size of most lenses is of the same order as the contamination products enabling them to become impregnated into matrix. However molecules of similar charge to mass ratio but with different molecular sizes can be separated.

With low voltage and current and the relatively large volume of buffer, heating effects are negligible. Platinum electrodes are preferred because they are inert. During the passage of the current electrolysis occurs at the electrodes. Any effects of electrolysis and pH changes are overcome by using a relatively large buffer volume and by the continual mixing due to slow circulation of the buffer solution. However, diffusion is minimal due to the applied voltage.

What I claim is:

1. A method of decontaminating and sterilizing a contact by electrophoresis, said method comprising the steps of:
   (i) establishing a unidirectional electric field between two electrodes in a buffer solution, and
   (ii) inserting a perforated holder containing said lens in the buffer solution in the electric field between the electrodes for a predetermined time, wherein said buffer solution has a pH between 8 and 9.

2. A method as claimed in claim 1 wherein said buffer solution has a pH of approximately 8.3 and comprises a dilution of a concentrate of boric acid, disodium edetate and tromethamine in relative proportions of approximately 0.808M, 0.029M and 0.825M respectively.

3. A buffer solution for use in an electrophoretic contact lens decontamination and sterilizing device, said buffer solution having a pH of approximately 8.3 and comprising a dilution of a concentrate of boric acid, disodium edetate and tromethamine in relative proportions of approximately 0.808M, 0.029M and 0.825M respectively.

* * * * *